United States Patent
Kaditz et al.

(10) Patent No.: US 10,964,412 B2
(45) Date of Patent: Mar. 30, 2021

(54) POPULATION-BASED MEDICAL RULES VIA ANONYMOUS SHARING

(71) Applicant: Q Bio, Inc, Millbrae, CA (US)

(72) Inventors: Jeffrey Howard Kaditz, Wilson, WY (US); Andrew Gettings Stevens, New York, NY (US)

(73) Assignee: Q Bio, Inc., San Carlos, CA (US)

( * ) Notice: Subject to any disclaimer, the term of this patent is extended or adjusted under 35 U.S.C. 154(b) by 1108 days.

(21) Appl. No.: 15/299,337

(22) Filed: Oct. 20, 2016

(65) Prior Publication Data

US 2017/0109475 A1    Apr. 20, 2017

Related U.S. Application Data

(60) Provisional application No. 62/244,159, filed on Oct. 20, 2015.

(51) Int. Cl.
  *G16H 10/60*  (2018.01)
  *G16H 40/67*  (2018.01)

(52) U.S. Cl.
  CPC ............ *G16H 10/60* (2018.01); *G16H 40/67* (2018.01)

(58) Field of Classification Search
  CPC ........ G16H 70/20; G16H 15/00; G16H 10/20; G16H 30/40; G16H 70/60; G16H 10/40;
  (Continued)

(56) References Cited

U.S. PATENT DOCUMENTS 4,729,892 A   3/1988 Beall
5,486,762 A   1/1996 Freedman et al.
(Continued)

FOREIGN PATENT DOCUMENTS

EP    3093677    11/2016
WO    2014205275 A1    12/2014
(Continued)

OTHER PUBLICATIONS

Hasenkam et al. "Prosthetic Heart Valve Evaluation by Magnetic Resonance Imaging." European Journal of Cardio-Thoracic Surgery 1999, pp. 300-305, 16, [Retrieved Aug. 25, 2016] <http://ejcts.oxfordjournals.org/content/16/3/300.full.pdf+html>.

(Continued)

*Primary Examiner* — Linh Giang Le
(74) *Attorney, Agent, or Firm* — Aurora Consulting LLC; Steven E. Stupp; Ashley Sloat

(57) ABSTRACT

A computer system may iteratively modify a local medical rule that is based on an initial sub-population. In particular, after information specifying the local medical rule and sharing instructions are received from a user of the computer system, the computer system may iteratively apply the local medical rule to one or more additional sub-populations that are associated with other users of the computer system based on the sharing instructions without sharing PHI associated with the initial sub-population. Then, the computer system may aggregate results for the one or more additional sub-populations, and may generate the population-based medical rule by modifying the local medical rule based on the aggregated results and one or more quality metrics. Moreover, the computer system may selectively provide the population-based medical rule to the user without sharing PHI associated with the one or more additional sub-populations.

20 Claims, 7 Drawing Sheets

(58) Field of Classification Search
CPC ........ G16H 10/65; G16H 20/10; G16H 20/40;
G16H 50/50; G16H 30/20; G16H 40/60;
G16H 80/00; G16H 20/60; G16H 20/70;
G16H 70/40; G16H 10/60; G16H 40/67;
G06Q 50/24; G06Q 10/00; G06Q 10/02;
G06Q 10/0631; G06Q 10/08; G06Q
10/087; G06Q 10/10; G06Q 20/4016;
G06Q 30/00; G06Q 30/0236; G06Q
30/0243; G06Q 30/0247; G06Q 30/0264;
G06Q 30/0267; G06Q 30/0269; G06Q
30/0281; G06Q 30/0605; G06Q 30/0641;
G06Q 30/08; G06Q 50/12; G06Q 50/28;
A61B 17/00
See application file for complete search history.

(56) References Cited

U.S. PATENT DOCUMENTS

| | | | |
|---|---|---|---|
| 5,793,210 A | 8/1998 | Pla et al. | |
| 6,084,408 A | 7/2000 | Chen | |
| 6,148,272 A | 11/2000 | Bergstrom et al. | |
| 6,392,409 B1 | 5/2002 | Chen | |
| 7,924,002 B2 | 4/2011 | Lu | |
| 7,940,927 B2 | 5/2011 | Futa et al. | |
| 7,974,942 B2 | 7/2011 | Pomroy | |
| 8,432,165 B2 | 4/2013 | Weiger Senften | |
| 8,502,532 B2 | 8/2013 | Assmann | |
| 8,686,727 B2 | 4/2014 | Reddy et al. | |
| 8,723,518 B2 | 5/2014 | Seiberlech et al. | |
| 8,736,265 B2 | 5/2014 | Boernert et al. | |
| 9,513,359 B2 | 12/2016 | Koch | |
| 9,514,169 B2 | 12/2016 | Mattsson | |
| 2002/0049612 A1* | 4/2002 | Jaeger | G06F 19/325 705/2 |
| 2002/0155587 A1 | 10/2002 | Opalsky | |
| 2002/0177771 A1 | 11/2002 | Guttman et al. | |
| 2003/0210043 A1 | 11/2003 | Freedman | |
| 2004/0073460 A1* | 4/2004 | Erwin | G06F 19/325 705/2 |
| 2005/0137476 A1 | 6/2005 | Welland | |
| 2005/0181466 A1 | 8/2005 | Dambinova | |
| 2008/0065665 A1 | 3/2008 | Pomroy | |
| 2008/0081375 A1 | 4/2008 | Tesiram et al. | |
| 2008/0082834 A1 | 4/2008 | Mattsson | |
| 2009/0006283 A1* | 1/2009 | Labrie | G06F 16/215 706/12 |
| 2009/0315561 A1 | 12/2009 | Assmann | |
| 2010/0131518 A1 | 5/2010 | Elteto | |
| 2010/0142823 A1 | 6/2010 | Wang et al. | |
| 2010/0177188 A1 | 7/2010 | Kishima | |
| 2010/0189328 A1 | 7/2010 | Boernert et al. | |
| 2010/0244827 A1 | 9/2010 | Hennel | |
| 2010/0306854 A1 | 12/2010 | Neergaard | |
| 2011/0044524 A1* | 2/2011 | Wang | G01R 33/54 382/131 |
| 2011/0095759 A1 | 4/2011 | Bhattacharya et al. | |
| 2011/0166484 A1 | 7/2011 | Virta | |
| 2011/0288877 A1* | 11/2011 | Ofek | G06Q 10/10 705/2 |
| 2012/0101846 A1* | 4/2012 | Gotthardt | G06Q 50/24 705/3 |
| 2012/0124161 A1 | 5/2012 | Tudwell et al. | |
| 2013/0085406 A1* | 4/2013 | Gunderson | A61B 5/7264 600/518 |
| 2013/0275718 A1 | 10/2013 | Ueda | |
| 2013/0294669 A1 | 11/2013 | El-Baz | |
| 2013/0338930 A1 | 12/2013 | Senegas | |
| 2014/0062475 A1 | 3/2014 | Koch | |
| 2014/0336998 A1 | 11/2014 | Cecchi | |
| 2015/0003706 A1 | 1/2015 | Eftestol et al. | |
| 2015/0032421 A1 | 1/2015 | Dean et al. | |
| 2015/0040225 A1 | 2/2015 | Coates et al. | |
| 2015/0089574 A1 | 3/2015 | Mattsson | |
| 2015/0154646 A1* | 6/2015 | Mishra | G06Q 50/24 705/3 |
| 2016/0007968 A1 | 1/2016 | Sinkus | |
| 2016/0127123 A1 | 5/2016 | Johnson | |
| 2017/0011514 A1 | 1/2017 | Westerhoff | |
| 2017/0038452 A1 | 2/2017 | Trzasko | |

FOREIGN PATENT DOCUMENTS

| | | |
|---|---|---|
| WO | WO-2015183792 | 12/2015 |
| WO | WO-2016073985 | 5/2016 |

OTHER PUBLICATIONS

Nestares, et al. "Robust Multiresolution Alignment of MRI Brain Volumes." Magnetic Resonance in Medicine 2000, pp. 705-715, [Retrieved Aug. 27, 2016] <http://web.mit.edu/ImagingPubs/Coregistration/nestares_heeger_coreg.pdf>.

International Search Report and Written Opinion dated Nov. 28, 2016 re PCT/US16/51204.

International Search Report and Written Opinion dated Sep. 19, 2016 re PCT/US16/040578.

International Search Report and Written Opinion dated Sep. 19, 2016 re PCT/US16/040215.

"International Application Serial No. PCT/US2016/040215, International Preliminary Report on Patentability and Written Opinion dated Jan. 9, 2018, Other Description Jan. 9, 2018".

"Kwan et al: "MRI Simulation-Based Evaluation of Image-Processing and Classification Methods" IEEE Transactions on Medical Imaging. vol. 18 No. 11, Nov. 1999, , Final office action dated Jun. 28, 2018", 13 pgs.

"Siemens. Magnetic Resonance Imaging. (Dec. 2012) [retrieved on Jun. 27, 2017, https://w5.siemens.com/web/ua/ru/medecine/detection_diagnosis/magnetic_resonans/035-15-MRI-scaners/Documents/mri-magnetom-family_brochure-00289718.pdf] p. 6-8, 13, 15-16, PCT search report dated Jul. 19, 2017".

"Gualda et al. SPIM-fluid: open source light-sheet based platform for high-throughput imaging. Biomed Opt Express (Nov. 1, 2015} vol. 6, No. 11, pp. 4447-4456, p. 4448 para 2-3, p. 4450, para 2, PCT search report dated Jul. 19, 2017".

"International Application Serial No. PCT/US2017/035071, International Search Report dated Aug. 22, 2017, PCT search report dated Aug. 22, 2017", 2 pgs.

"International Application Serial No. PCT/US2017/035071, Written Opinion dated Aug. 22, 2017, PCT report opinion dated Aug. 22, 2017", 7 pgs.

"International Application Serial No. PCT/US2017/035073, International Search Report dated Aug. 11, 2017, PCT search report dated Aug. 11, 2017", 2 pgs.

"International Application Serial No. PCT/US2017/035073, Written Opinion dated Aug. 11, 2017, PCT report opinion dated Aug. 11, 2017", 6 pgs.

"G. Schultz, "Magnetic Resonance Imaging with Nonlinear Gradient Fields: Signal Encoding and Image Reconstruction" Springer Verlag, New York, 2013), Chapter 2, pp. 1-10., Other Description Oct. 23, 2017".

"International Application Serial No. PCT/US2017/022842, Written Opinion dated May 23, 2017, PCT report opinion dated May 23, 2017", 4 pgs.

"International Application Serial No. PCT/US2017/022842, International Search Report dated May 23, 2017, PCT search report dated May 23, 2017", 2 pgs.

* cited by examiner

POPULATION-BASED MEDICAL RULES VIA ANONYMOUS SHARING

CROSS-REFERENCE TO RELATED APPLICATION

The is application claims priority under 35 U.S.C. § 119(e) to: U.S. Provisional Application Ser. No. 62/244,159, entitled "System and Method for Contextually Sensitive Notifications for Medical Practitioners and Co-Anonymized Studies," by Jeffrey H. Kaditz and Andrew G. Stevens, filed on Oct. 20, 2015, the contents of which are herein incorporated by reference.

BACKGROUND

Field

The described embodiments relate to techniques for generating medical rules. In particular, the described embodiments relate to techniques for generating medical rules based on iterative analysis of the impact of a medical rule in a population without sharing Protected Health Information (PHI) associated with individuals in the population.

Related Art

Modern medicine has achieved significant improvements in individual health, quality of life and lifespans. These laudable public-health results have been achieved using a rigorous process that includes double-blind clinical trials and peer-reviewed publication of results. In principle, this evidence-based approach to determining medical knowledge offers the exciting prospect of further reductions in morbidity and mortality.

In practice, there are drawbacks to the existing evidence-based approach. In particular, it can take months or even years to plan and then conduct a clinical trial. Similarly, the lead time for a subsequent publication in a peer-reviewed journal can be as long as twelve to eighteen months. Consequently, the temporal sampling with which medical knowledge grows is often limited. This can make it difficult to adapt medical knowledge to time varying or transient phenomena.

In addition, many published results in peer-reviewed journals subsequently proves either to be difficult to reproduce or incorrect. In the context of the aforementioned low temporal sampling rate, this means that it can take many years for these errors in medical knowledge to be identified and corrected. Therefore, while the existing approach for determining medical knowledge has resulted in many achievements, it also has limitations that constrain medical knowledge, which can, paradoxically, adversely impact patient health, patient trust and patient satisfaction.

SUMMARY

The described embodiments relate to a computer system that dynamically generates a population-based medical rule via anonymous sharing of a local medical rule. This computer system includes: a processor that executes a program module; and memory that stores the program module. During operation, the processor executing the program module receives, from a user, information specifying the local medical rule associated with an initial sub-population and sharing instructions that specify other users that can access the local medical rule. Then, the processor iteratively: applies the local medical rule to one or more additional sub-populations without sharing PHI associated with the initial sub-population, where the one or more additional sub-populations are associated with at least some of the other users; aggregates results associated with the local medical rule for the one or more additional sub-populations; and generates the population-based medical rule by modifying the local medical rule based on the aggregated results and one or more quality metrics. After generating the population-based medical rule, the processor selectively provides the population-based medical rule to the user without sharing PHI associated with the one or more additional sub-populations.

Note that applying the local medical rule to one or more additional sub-populations may involve retrospective analysis using medical records associated with the one or more additional sub-populations. For example, the retrospective analysis may involve reanalyzing previously acquired measurements based on a stored measurement configuration that was used to acquire the measurements. Alternatively or additionally, applying the local medical rule to the one or more additional sub-populations may involve using the local medical rule during future clinical encounters with individuals in the one or more additional sub-populations.

Moreover, the local medical rule may include one or more diagnostic criteria and/or a treatment protocol.

Furthermore, the processor may continuously or periodically perform the operations of applying, aggregating and generating for the population-based medical rule.

Additionally, selectively providing the population-based medical rule may involve providing a notification to the user.

In some embodiments, the processor provides, to the other users, notifications about the local medical rule in response to the sharing instructions. In response to receiving an opt-in instruction from one of the other users, the processor may include a particular sub-population in the one or more additional sub-populations.

Note that the user and the other users may include healthcare providers and/or healthcare researchers.

Moreover, the local medical rule may include a query.

Furthermore, the population-based medical rule may be editable. When an editing instruction for the population-based medical rule is received from another user, the revised population-based medical rule may be retroactively applied to medical records associated with the initial sub-population and/or the one or more additional sub-populations. Alternatively or additionally, the revised population-based medical rule may be prospectively applied during further clinical encounters with individuals in the initial sub-population and/or one or more additional sub-populations. Then, the processor may aggregate second results associated with the revised population-based medical rule and may determine an updated population-based medical rule based on the aggregated second results and the one or more quality metrics.

Another embodiment provides a computer-program product for use with the computer system. This computer-program product includes instructions that, when executed by a processor, cause a computer system to perform at least some of the aforementioned operations.

Another embodiment provides a method for dynamically generating a population-based medical rule via anonymous sharing of a local medical rule.

The preceding summary is provided as an overview of some exemplary embodiments and to provide a basic understanding of aspects of the subject matter described herein. Accordingly, the above-described features are merely examples and should not be construed as narrowing the scope or spirit of the subject matter described herein in any way. Other features, aspects, and advantages of the subject

BRIEF DESCRIPTION OF THE FIGURES

Note that like reference numerals refer to corresponding parts throughout the drawings. Moreover, multiple instances of the same part are designated by a common prefix separated from an instance number by a dash.

DETAILED DESCRIPTION

Figure 1:
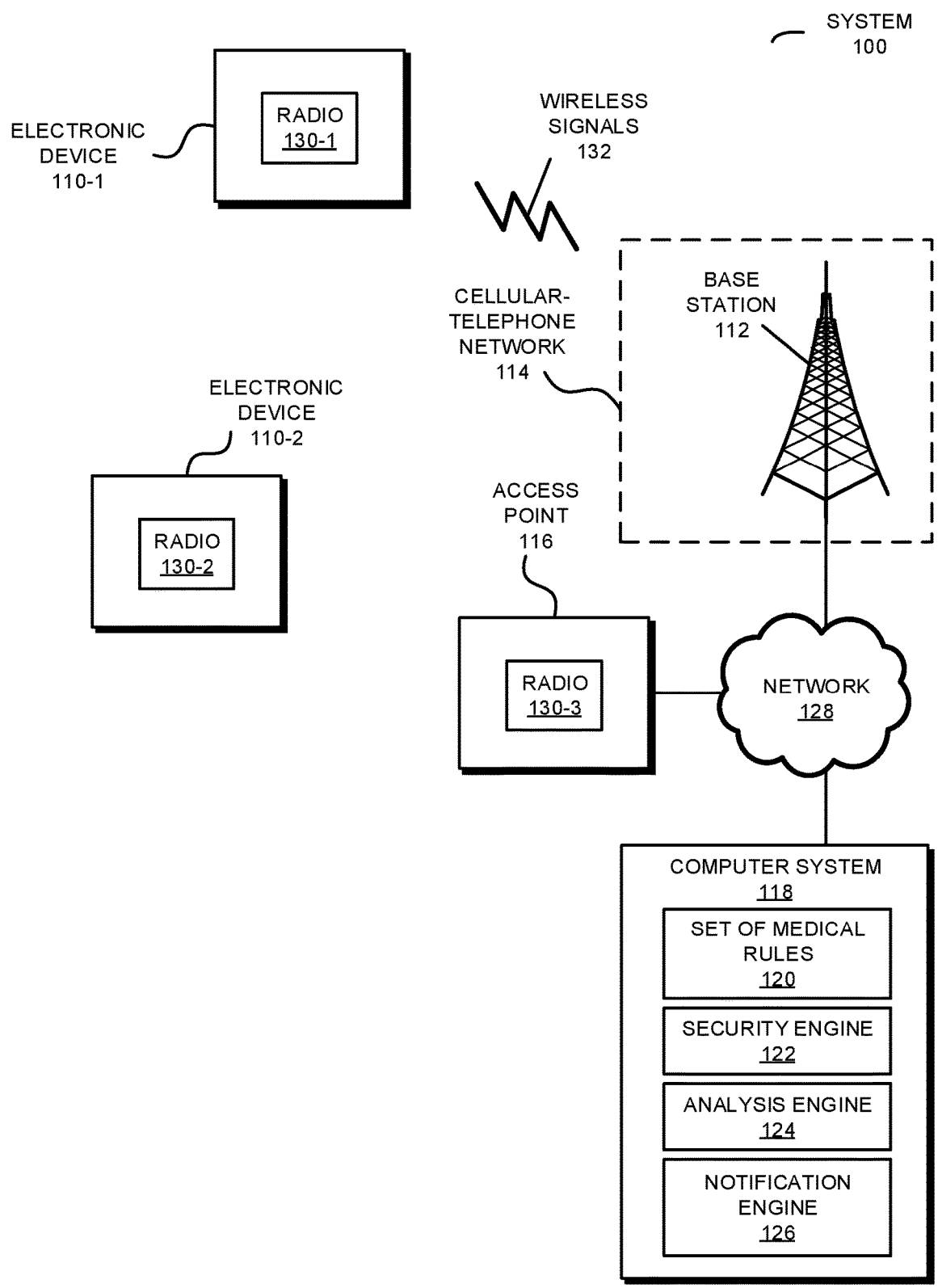
FIG. 1 is a block diagram illustrating a system that generates medical rules in accordance with an embodiment of the present disclosure.

In order to rapidly generate and selectively adapt a population-based medical rule on an on-going basis, a computer system may iteratively modify a local medical rule that is based on an initial sub-population. In particular, after information specifying the local medical rule and sharing instructions are received from a user of the computer system, the computer system may iteratively apply the local medical rule to one or more additional sub-populations that are associated with other users of the computer system based on the sharing instructions without sharing PHI associated with the initial sub-population. Then, the computer system may aggregate results for the one or more additional sub-populations, and may generate the population-based medical rule by modifying the local medical rule based on the aggregated results and one or more quality metrics. Moreover, the computer system may selectively provide the population-based medical rule to the user without sharing PHI associated with the one or more additional sub-populations.

By dynamically generating the population-based medical rule while protecting PHI, this analysis technique may facilitate learning in large populations while complying with laws and regulations (e.g., PHI in general is covered by the Health Insurance Portability and Accountability Act or HIPAA, while electronic PHI, such as medical records, is covered by the HIPAA Security Rule) and respecting patient privacy. In the process, the analysis technique may increase the accuracy of the medical rule (and, more generally, medical knowledge) while increasing the temporal sampling, thereby addressing many of the limitations in the existing evidence-based approach that is presently used in healthcare and healthcare research. Moreover, the analysis technique can decouple measurements from analysis, thereby facilitating, on an on-going basis, both retrospective analysis of existing medical records and prospective analysis of current patient treatment. In these ways, the analysis technique may facilitate further improvements in patient health, patient trust and patient satisfaction, with a commensurate impact on the cost of medical care.

In the discussion that follows, an individual or a user may be a person. Moreover, the analysis technique may be used by any type of organization, such as a business, which should be understood to include for-profit corporations, non-profit corporations, groups (or cohorts) of individuals, sole proprietorships, government agencies, partnerships, etc. While the analysis technique may be used in a wide variety of applications, in the discussion that follows the analysis technique is used in healthcare to generate population-based medical rules. Note that a medical rule may, in general, be used to diagnosis a trait or a condition (such as the presence of a disease) and/or may be used to guide treatment. Therefore, a medical rule may include a set of diagnostic criteria (such as one or more symptoms, vital signs, tests to perform, test results, etc. that are associated with a trait or a condition) and/or a set of treatment protocols (such as one or more medical procedures, pharmaceuticals, etc., as well as an order for their use when treating a trait or a condition).

Furthermore, in the discussion that follows, electronic devices and/or components in a system that includes the computer system may communicate using a wide variety of communication protocols. For example, the communication may involve wired or wireless communication. Consequently, the communication protocols may include: an Institute of Electrical and Electronics Engineers (IEEE) 802.11 standard (which is sometimes referred to as 'Wi-Fi®,' from the Wi-Fi Alliance of Austin, Tex.), Bluetooth® (from the Bluetooth Special Interest Group of Kirkland, Wash.), another type of wireless interface (such as another wireless-local-area-network interface), a cellular-telephone communication protocol (e.g., a 3G/4G/5G communication protocol, such as UMTS, LTE), an IEEE 802.3 standard (which is sometimes referred to as 'Ethernet'), etc. In the discussion that follows, Ethernet and Wi-Fi and/or a cellular telephone communication protocol are used as illustrative examples.

Communication among electronic devices is shown in FIG. 1, which presents a block diagram illustrating a system 100 that dynamically generates a medical rule. In particular, system 100 includes one or more electronic devices 110 (such as cellular telephones or portable electronic devices, computers, etc.), optional base station 112 in cellular-telephone network 114, optional access point 116, and computer system 118 (which are sometimes collectively referred to as 'components' in system 100). Moreover, computer system 118 may include: a set of medical rules 120 (which may be stored in memory or a computer-readable medium, which may include a biovault), a security engine (or module) 122, an analysis engine (or module) 124 and a notification engine (or module) 126. In some embodiments, the set of medical rules 120 includes a block chain, i.e., a distributed database that maintains a continuously growing list of records (with data, individual transactions, the results of any blockchain executables and/or programs, as well as timestamps and links to one or more previous blocks) secured from tampering and revision, so that a history of updates and changes to the medical rules can be maintained. Therefore, changes to the set of medical rules 120 may be appended to the existing set of medical rules 120.

Note that components in system 100 may communicate with each other via a network 128, such as the Internet, a cellular-telephone network and/or a wireless local area network (WLAN). In embodiments where the communication involves wireless communication, the wireless communication includes: transmitting advertising frames on wireless channels, detecting another component in system 100 by scanning wireless channels, establishing connections (for example, by transmitting association requests), and/or transmitting and receiving packets (which may include information for inclusion in the set of medical rules 120, requests for access to information in the set of medical rules 120, notifications, etc.).

Moreover, as described further below with reference to FIG. 6, electronic devices 110, optional base station 112, optional access point 116 and computer system 118 may include subsystems, such as a networking subsystem, a memory subsystem and a processor subsystem. In addition, electronic devices 110, optional base station 112, optional access point 116 and computer system 118 may include radios 130 in the networking subsystems. More generally, the components can include (or can be included within) any electronic devices with the networking subsystems that enable these components to communicate with each other. Note that wireless communication can comprise transmitting advertisements on wireless channels to enable a pair of components to make initial contact or detect each other, followed by exchanging subsequent data/management frames (such as association requests and responses) to establish a connection, configure security options (e.g., Internet Protocol Security), transmit and receive packets or frames via the connection, etc.

Moreover, as can be seen in FIG. 1, wireless signals 132 (represented by jagged lines) are transmitted by radios 130 in the components. For example, radio 130-1 in electronic device 110-1 may transmit information (such as packets) using wireless signals. These wireless signals may be received by radios 130 in one or more of the other components, such as by optional base station 112 or optional access point 116. This may allow electronic device 110-1 to communicate information to optional base station 112 or optional access point 116, and thus, to computer system 118.

In the described embodiments, processing a packet or frame in a component may include: receiving the wireless signals with the packet or frame; decoding/extracting the packet or frame from the received wireless signals to acquire the packet or frame; and processing the packet or frame to determine information contained in the packet or frame (such as information for inclusion in the set of medical rules 120, a request or query, a notification, etc.).

Note that the communication between at least any two of the components in system 100 may be characterized by one or more of a variety of performance metrics, such as: a received signal strength indication (RSSI), a data rate, a data rate for successful communication (which is sometimes referred to as a 'throughput'), an error rate (such as a retry or resend rate), a mean-square error of equalized signals relative to an equalization target, intersymbol interference, multipath interference, a signal-to-noise ratio, a width of an eye pattern, a ratio of number of bytes successfully communicated during a time interval (such as 1-10 s) to an estimated maximum number of bytes that can be communicated in the time interval (the latter of which is sometimes referred to as the 'capacity' of a communication channel or link), and/or a ratio of an actual data rate to an estimated data rate (which is sometimes referred to as 'utilization').

One or more users (such as an individual or a group of individuals) may use electronic device 110-1 to request, via network 128, information in the set of medical rules 120. In particular, one or more users (such as a user of electronic device 110-1) may provide a request for information associated with a particular medical rule (such as a diagnostic criteria and/or a treatment protocol for a disease). If the one or more users are authorized to access the particular medical rule (e.g., based on sharing instructions associated with the medical rule, which were provided when the medical rule was initially defined or provided by one of the users), computer system 118 may securely and anonymously provide, via network 128, the requested information (or a pointer to the requested information) to electronic device 110-1 via a user interface.

Moreover, notification engine 126 may selectively provide, via network 128, notifications to one or more of electronic devices 110 and, thus, to the associated users of these electronic devices. For example, the notifications may indicate that a revised or updated population-based medical rule is available (such as an updated population-based medical rule that has sufficient accuracy or that is confirmed, to a particular statistical significance, as correct). If a user activates a virtual link that is associated with or included in a notification, computer system 118 may securely and anonymously provide information that specifies the revised or updated population-based medical rule (or that summarizes its efficacy, sensitivity, and/or specificity) to at least a user via a user interface on one of electronic devices 110.

In some embodiments, information in the set of medical rules 120 may be, at least in part, encrypted or securely hashed (such as using SHA-256) and stored separately from the encryption key(s) or the secure hashing function(s). For example, encrypted information and the associated public encryption keys may be stored in the set of medical rules 120, and the corresponding private encryption keys may be stored separately. Therefore, when computer system 118 provides information in the set of medical rules 120, security engine 122 may also provide access information, such as a public encryption key or information that specifies a secure hashing function.

Furthermore, as discussed further below with reference to FIGS. 2 and 3, one or more users (such as a healthcare provider and/or a healthcare researcher) may use one of electronic devices 110 (such as electronic device 110-1) to provide, via network 128, information to computer system 118 for inclusion in one or more records in set of medical rules 120 and/or in one or more associated data structures (such as in one or more medical records). For example, the information may include a local medical rule associated with an initial sub-population and sharing instructions that specify other users in system 100 (such as other healthcare providers and/or other healthcare researchers) that can access the local medical rule. In response to receiving this information, security engine 122 may securely store the information in the one or more records. For example, this may include security engine 122 encrypting and/or securely hashing the information.

In some embodiments, security engine 122 may securely store information by performing operations, such as: scrambling timestamps (and, more generally, words or values in a timeline); substituting replacement fields (such as random or pseudorandom alphanumeric information) for fields in set of medical rules 120 (such as based on predefined substitution rules, the cardinality of the fields and, more generally, the information value of the fields), and/or generating artificial or fictitious records based on, at least in part the set of medical rules 120 so that at least some of the phrases or values in the combination of the artificial records and the set of medical rules 120 have uniform distributions or frequencies of occurrence. Note that security engine 122 may randomly or pseudo-randomly order the positions of the artificial records in the set of medical rules 120.

After receiving the information specifying the local medical rule, computer system 118 may anonymously share the local medical rule with one or more other users specified in the sharing instructions associated with the local medical rule. For example, notification engine 126 may provide, via network 128, notifications to electronic devices 110 associated with the one or more other users about the local medical rule in response to the sharing instructions. Subsequently, computer system 118 may receive, via network 128, an opt-in instruction from an electronic device associated with one of the other users (such as when this user accepts the notification and requests access to the local medical rule by, e.g., clicking on or activating a link that is associated with the notification). In response, analysis engine 124 may include a particular sub-population associated with the one of the other users in one or more additional sub-populations that will be analyzed using the local medical rule.

Then, analysis model 124 may perform analysis of the one or more additional sub-populations based on the local medical rule. For example, analysis engine 124 may iteratively: apply the local medical rule to one or more additional sub-populations without sharing PHI associated with the initial sub-population (such as by removing or excluding PHI from the specified local medical rule or the associated results of the local medical rule when applied to the initial sub-population); aggregate results associated with the local medical rule for the one or more additional sub-populations; and generate the population-based medical rule by modifying the local medical rule based on the aggregated results and one or more quality metrics (such as a convergence criterion, a confidence interval or an accuracy of the local medical rule as applied to the one or more additional sub-populations).

Moreover, as discussed previously, after generating the population-based medical rule, computer system 118 may anonymously share the population-based medical rule with the user that originally specified or provided the local medical rule. For example, notification engine 126 may provide, via network 128, a notification to the user about the population-based medical rule. Subsequently, computer system 118 may receive, via network 128, an opt-in instruction from the user (such as when the user accepts the notification and requests access to the population-based medical rule by, e.g., clicking on or activating a link that is associated with the notification). In response, computer system 118 may selectively provide the population-based medical rule (or information that specifies the population-based medical rule and/or that summarizes its efficacy, sensitivity, and/or specificity) to the user without sharing PHI associated with the one or more additional sub-populations (such as by removing or excluding PHI from the population-based medical rule or the associated results of the population-based medical rule when applied to the one or more additional sub-populations). Similarly, the population-based medical rule may be anonymously shared with the one or more other users.

Note that applying the local medical rule to one or more additional sub-populations may involve retrospective analysis using medical records associated with the one or more additional sub-populations. In order to facilitate the re-analysis, measurements may be separated from the corresponding analysis or results. In particular, the medical records in or associated with system 100 may include the measurement data, the analyzed results (such as a diagnostic opinion, e.g., a radiology report) and information about the measurement technique used to determine the current measurement results, such as information that specifies a configuration of a machine or equipment that was used to acquire the measurement (which is sometimes referred to as a 'measurement configuration' or 'measurement instructions'). Therefore, if it is subsequently determined that the measurement configuration was sub-optimal or could be improved, analysis engine 124 may apply a corresponding medical rule retrospectively to the measurement data based on the stored measurement configuration to revise the analyzed results. In this way, the analysis results may be revised or updated as medical knowledge (in the form of the medical rules) is improved or expanded.

As described further below with reference to FIG. 5, in some embodiments the re-analysis involves using a magnetic-resonance (MR) model of a biological organism based on voxel parameters (such as type of nuclei, densities, spin-lattice ($T_1$) and spin-spin ($T_2$) relaxation times, etc.) and a new measurement configuration (such as scanning instructions, applied magnetic field(s), etc.) to determine simulated MR signals (which are sometimes referred to as calculated MR signals or estimated MR signals) for the biological organism. For example, the simulated MR signals may be determined using an invariant MR signature and the new measurement configuration. More generally, the re-analysis may involve using a tensor-field map of the biological organism based on voxel parameters and a new measurement configuration to determine simulated measurement data. The resulting simulated measurement data may be re-analyzed based on one of the set of medical rules 120 to determine new analysis results.

Alternatively or additionally, applying the local medical rule to the one or more additional sub-populations may involve using the local medical rule during future clinical encounters with individuals in the one or more additional sub-populations (i.e., prospectively). Thus, in these embodiments, analysis engine 126 may provide, via network 128, the local medical rule to electronic devices 110 associated with the one or more other users.

In some embodiments, the local medical rule may include a query, such as whether a particular diagnostic criterion or a treatment protocol results in better or worse patient outcomes.

Moreover, instead of converging to a solution and then stopping, analysis engine 124 may continuously or periodically (such as daily, weekly or monthly) perform the operations of applying, aggregating and generating for the population-based medical rule. In this way, the population-based medical rule may be tested and, if appropriate, evolved or adapted based on its performance. This approach may allow computer system 118 to assess, on an on-going basis, the efficacy of a population-based medical rule and to change the population-based medical rule to address challenges such as new medical knowledge and/or dynamic or transient phenomena (e.g., a new or emergent disease). Thus, the analysis technique may provide on-going monitoring and learning.

Furthermore, the population-based medical rule may be editable. When computer system 118 receives, via network 128, an editing instruction for the population-based medical rule from one of electronic devices 110 associated with another user, analysis engine 124 may apply the revised population-based medical rule retroactively to medical records associated with the initial sub-population and/or the one or more additional sub-populations. Alternatively or additionally, the analysis engine 124 may prospectively apply the revised population-based medical rule during further or subsequent clinical encounters with individuals in the initial sub-population and/or one or more additional sub-populations. Then, analysis engine 124 may aggregate second results associated with the revised population-based medical rule and may determine an updated population-based medical rule based on the aggregated second results and the one or more quality metrics (such as a convergence criterion, a confidence interval or an accuracy of the revised medical rule as applied to the initial sub-population and/or the one or more additional sub-populations).

In some embodiments, one or more of the users may use electronic devices 110 to provide, via network 128, ratings for the medical rules to computer system 118. These evolving ratings may be used to dynamically assess the local medical rule and/or the population-based medical rules, and thus may be used to determine updates or revisions to the medical rules.

In these ways, computer system 118 may dynamically generate population-based medical rules while protecting PHI, may facilitate active learning, may improve patient outcomes and may reduce medical costs.

Note that the analysis technique may be used to generate and apply medical rules that are used in conjunction with a wide variety of non-invasive measurement techniques. In the discussion that follows MR techniques, and in particular magnetic-resonance imaging (MRI) and magnetic-resonance spectroscopy (MRS), are used as illustrative examples. However, the measurement technique may include: an MR technique, computed tomography, ultrasound imaging, x-ray imaging, positron emission spectroscopy, electron spin resonance, optical/infrared spectroscopy (e.g., to determine a complex index of refraction at one or more wavelengths), an electrical measurement (such as an electrocardiogram, an electromyogram, an electroencephalogram, etc.), proton beam, photoacoustic imaging, other non-destructive measurements (such as radar or millimeter-wave scanning), activity or behavior data for the biological organism (such as data capture using a wearable electronic device), measurements performed by nano particles in the biological organism, chemical composition of fluids (such as blood) measured at arbitrary locations in the biological organism non-destructively or by drawing a blood sample (e.g., using microfluidics), height, weight, a vital sign (pulse, respiration, temperature, blood pressure, etc.), genetic or genomic information (such as sequencing, next-generation sequencing, RNA sequencing, epigenetic information, etc.), quantitative tensor field maps, medical images, blood or lab tests, microbiome analysis, urine analysis, stool analysis, thermal-imaging readings, optical images, body impedance, biopsies, another quantitative or qualitative characteristic or property of the biological organism, etc.

Moreover, the MR technique may include quantitative analysis of MR scans such as MR fingerprints of the biological organism that are magnetic-field invariant (which are sometimes referred to as 'magnetic-field-invariant MR signatures' or 'invariant MR signatures'). The invariant MR signatures may describe the dynamic MR responses of voxels at 3D positions in the one or more biological organisms at arbitrary magnetic-field strengths. Moreover, the invariant MR signatures may be independent of the MR scanners, as well as the specific scanning instructions (e.g., magnetic-field strengths and/or pulse sequences), used to acquire MR signals in a variation on MRF (which is sometimes referred to as 'quantitative MRF' or QMR-X) that were then used to determine the invariant MR signatures. An invariant MR signature may be determined by iteratively converging MR signals of one or more types of nuclei in the biological organism, which were acquired by an MR scanner based on scanning instructions, with simulated MR signals (which are sometimes referred to as calculated MR signals or estimated MR signals) for the biological organism that are generated using an MR model and the scanning instructions.

Furthermore, the MR technique may include: MRI, MRS, magnetic-resonance spectral imaging (MRSI) magnetic-resonance thermometry (MRT), magnetic-resonance elastography (MRE), MR fingerprinting (MRF), magnetic-field relaxometry, diffusion-tensor imaging and/or another MR technique (such as functional MRI, metabolic imaging, molecular imaging, blood-flow imaging, etc.). Note that these MR techniques are each a form of quantitative tensor-field mapping.

In particular, 'MRI' should be understood to include generating images (such as 2D slices) or maps of internal structure in a sample (such as anatomical structure in a biological sample, e.g., a tissue sample or a patient) based on the dynamic response of a type of nuclear spin (such protons or the isotope $^1$H) in the presence of a magnetic field, such as a non-uniform or spatially varying external magnetic field (e.g., an external magnetic field with a well-defined spatial gradient). Moreover, MRS should be understood to include determining chemical composition or morphology of a sample (such as a biological sample) based on the dynamic response of multiple types of nuclear spins (other than or in addition to $^1$H) in the presence of a magnetic field, such as a uniform external magnetic field.

Moreover, 'MRSI' should be understood to include generating images or maps of internal structure and/or chemical composition or morphology in a sample using MRS in the presence of a magnetic field, such as a non-uniform or spatially varying external magnetic field. For example, in MRSI the measured dynamic response of other nuclei in addition to $^1$H are often used to generate images of the chemical composition or the morphology of different types of tissue and the internal anatomy of the biological organism.

Furthermore, in contrast with existing approaches to MRI or MRSI that usually provide qualitative or 'weighted' measurements of a limited set of properties, 'MRF' should be understood to include quantitative measurements of the properties of a sample by acquiring signals representing a dynamic or time-dependent magnetization or MR trajectory (such as in k-space) from different materials in a sample using a pseudorandom pulse sequence. In particular, instead of using repeated, serial acquisition of data to characterize individual parameters that are of interest, in MRF signals from different materials or tissues are often acquired using a pseudorandom pulse sequence to determine a unique signal or 'fingerprint' (e.g., a time-dependent magnetization or MR trajectory). The resulting unique fingerprint of the sample is, in general, a function of multiple material properties under investigation. For example, MRF can provide high-quality quantitative maps of: a spin-lattice relaxation time $T_1$ (which is the time constant associated with the loss of signal intensity as components of the nuclear-spin magnetization vector relax to be parallel with the direction of an external magnetic field), a spin-spin relaxation time $T_2$ (which is the time constant associated with broadening of the signal during relaxation of components of the nuclear-spin magnetization vector perpendicular to the direction of the external magnetic field), proton density (and, more generally, the densities of one or more type of nuclei) and diffusion (such as components in a diffusion tensor).

Note that 'magnetic-field relaxometry' (such as $B_0$ relaxometry with the addition of a magnetic-field sweep) may involve acquiring MR images at different magnetic-field strengths. These measurements may be performed on the fly or dynamically (as opposed to performing measurements at a particular magnetic-field strength and subsequently cycling back to a nominal magnetic-field strength during readout, i.e., a quasi-static magnetic-field strength). For example, the measurements may be performed using untuned radio-frequency (RF) coils or a magnetometer so that measurements at the different magnetic-field strengths can be performed in significantly less time.

Additionally, 'MRE' should be understood to include measuring the stiffness of a sample using MRI by sending mechanical waves (such as sheer waves) through a sample, acquiring images of the propagation of the shear waves, and processing the images of the shear waves to produce a quantitative mapping of the sample stiffness (which are sometimes referred to as 'elastograms') and/or mechanical properties (such as rigidity, density, tensile strength, etc.).

Moreover, 'MRT' should be understood to include measuring maps of temperature change in a sample using MRI.

Note that a biological organism may include a tissue sample from an animal or a person (i.e., a portion of the animal or the person). For example, the tissue sample may have been previously removed from the animal or the person. In some embodiments, the tissue sample is a pathology sample, such as a biopsy sample. Thus, the tissue sample may be formalin fixed-paraffin embedded. However, in other embodiments a biological organism may be in the animal or the person (i.e., an in-vivo sample) and/or the measurement technique involves whole-body scans. Furthermore, the measurement technique may also be applied to inanimate (i.e., non-biological) samples of a wide variety of different materials. In the discussion that follows, the biological organism is a person or an individual, which is used as an illustrative example.

Although we describe the network environment shown in FIG. 1 as an example, in alternative embodiments, different numbers or types of electronic devices may be present. For example, some embodiments comprise more or fewer components. As another example, in another embodiment, different components are transmitting and/or receiving packets or frames.

Figure 2:
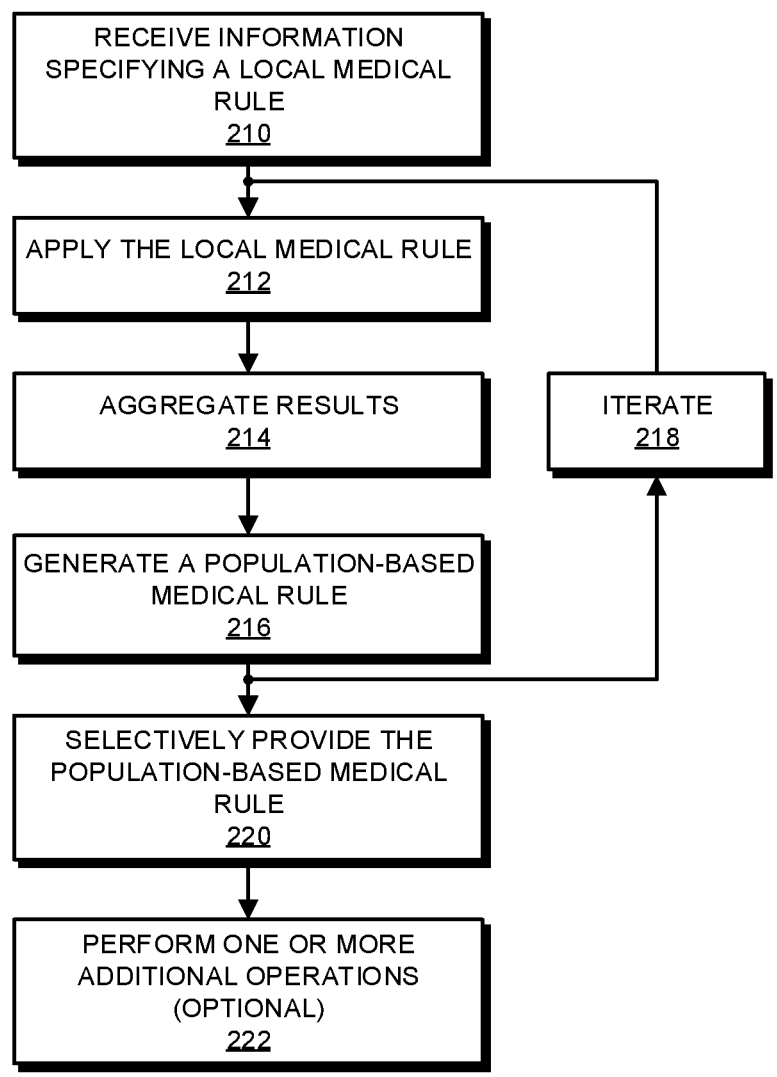
FIG. 2 is a flow diagram illustrating a method for generating medical rules using the system in FIG. 1 in accordance with an embodiment of the present disclosure.

FIG. 2 presents embodiments of a flow diagram illustrating method 200 for dynamically generates a population-based medical rule via anonymous sharing of a local medical rule, which may be performed by a computer system (such as computer system 118 in FIG. 1). During operation, the computer system (such as a processor executing a program module and, more generally, software executed in an environment, e.g., an operating system, of the computer system) may receive, from a user, information specifying the local medical rule (operation 210) associated with an initial sub-population and sharing instructions that specify other users that can access the local medical rule. For example, the local medical rule may include one or more diagnostic criteria and/or a treatment protocol. Note that the user and the other users may include healthcare providers and/or healthcare researchers. In some embodiments, the local medical rule includes a query, such as a categorical or a quantitative medical question.

Then, the computer system iteratively (operation 218): applies the local medical rule (operation 212) to one or more additional sub-populations without sharing PHI associated with the initial sub-population, where the one or more additional sub-populations are associated with at least some of the other users; aggregates results (operation 214) associated with the local medical rule for the one or more additional sub-populations; and generates the population-based medical rule (operation 216) by modifying the local medical rule based on the aggregated results and one or more quality metrics.

After generating the population-based medical rule (operation 216), such as after the one or more quality metrics are met, the computer system selectively provides the population-based medical rule (operation 220) to the user without sharing PHI associated with the one or more additional sub-populations. For example, selectively providing the population-based medical rule (operation 220) may involve providing a notification to the user if the population-based medical rule has sufficient accuracy (such as 0.1, 1 or 5%).

Note that applying (operation 212) the local medical rule to one or more additional sub-populations may involve retrospective analysis using medical records associated with the one or more additional sub-populations. For example, the retrospective analysis may involve reanalyzing previously acquired measurements based on a stored measurement configuration that was used to acquire the measurements. Alternatively or additionally, applying (operation 212) the local medical rule to the one or more additional sub-populations may involve using the local medical rule during future clinical encounters with individuals in the one or more additional sub-populations.

In some embodiments, the computer system performs one or more optional additional operations (operation 222). For example, the computer system may continuously or periodically perform the operations of applying (operation 212), aggregating (operation 214) and generating (operation 216) for the population-based medical rule. Moreover, prior to applying the local medical rule (operation 212), the computer system may provide, to the other users, notifications about the local medical rule in response to the sharing instructions. In response to subsequently receiving an opt-in instruction from one of the other users, the computer system may include a particular sub-population in the one or more additional sub-populations.

Furthermore, the population-based medical rule may be editable. When the computer system receives an editing instruction for the population-based medical rule from another user, the revised population-based medical rule may be retroactively applied to medical records associated with the initial sub-population and/or the one or more additional sub-populations. Alternatively or additionally, the revised population-based medical rule may be prospectively applied during further or additional clinical encounters with individuals in the initial sub-population and/or one or more additional sub-populations. Then, the computer system may aggregate second results associated with the revised population-based medical rule and may determine an updated population-based medical rule based on the aggregated second results and the one or more quality metrics.

In some embodiments of method 200, there may be additional or fewer operations. Moreover, the order of the operations may be changed, and/or two or more operations may be combined into a single operation.

Figure 3:
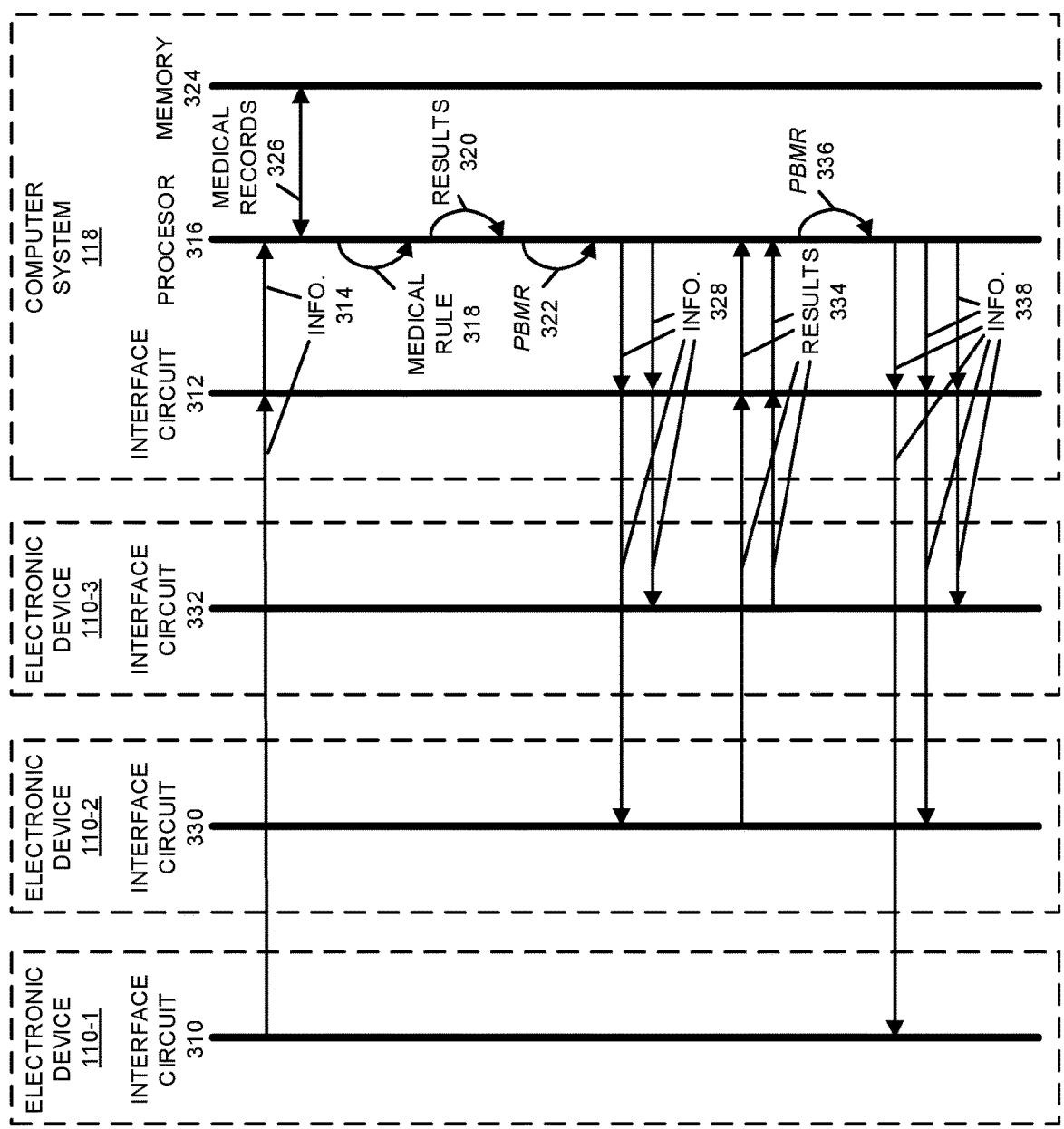
FIG. 3 is a drawing illustrating communication among components in the system in FIG. 1 in accordance with an embodiment of the present disclosure.

Embodiments of the analysis technique are further illustrated in FIG. 3, which presents a drawing illustrating communication among components in system 100 (FIG. 1). In particular, during the analysis technique, interface circuit 312 in computer system 118 may receive information 314 corresponding to or specifying a local medical rule 318 associated with an initial sub-population and sharing instructions from interface circuit 310 in electronic device 110-1. This information 314 may be provided to processor 316.

After receiving information 314, processor 316 may iteratively: apply the local medical rule 318 to one or more additional sub-populations without sharing PHI associated with the initial sub-population; aggregate results 320 associated with the local medical rule 318 for the one or more additional sub-populations; and generate a population-based medical rule (PBMR) 322 by modifying the local medical rule 318 based on the aggregated results 320 and one or more quality metrics.

For example, processor 316 may apply the local medical rule 318 by retrospectively analyzing medical records 326 associated with the one or more additional sub-populations, which are stored in memory 324.

Alternatively or additionally, processor 316 may instruct interface circuit 312 to provide information 328 corresponding to or specifying the local medical rule 318 to interface circuits 330 and 332 in electronic devices 110-2 and 110-3, so that other users may apply the local medical rule 318 to the one or more additional sub-populations, such as during future clinical encounters (such as doctors' appointments) of individuals in the one or more additional sub-populations. Then, interface circuit 312 may receive results 334 from electronic devices 110-2 and 110-3, and these results may be used by processor to generate the population-based medical rule 336.

After generating the population-based medical rule 322 or 336, processor 316 may instruct interface circuit 312 to selectively provide information 338 that corresponds to or that specifies the population-based medical rule 322 or 336 to one or more of electronic devices 110.

We now describe additional embodiments of the analysis technique. Advances in communications and medical technology are significantly increasing the amount of data available to healthcare providers. In addition, it is increasingly difficult for readers, such as physicians, to keep track of the large and ever-growing corpus of medical literature.

The disclosed analysis technique may be used to provide contextually sensitive notifications to healthcare providers and may facilitate co-anonymized studies (i.e., studies in which PHI is not shared in either direction). These capabilities may help healthcare providers to provide high-quality and improving care to their patients.

As described further below with reference to FIG. 4, the contextually sensitive notifications may include displaying one or more relevant scientific or medical papers (or links to the one or more relevant scientific or medical papers) in a user interface while a healthcare provider is reviewing the records of a patient. The relevancy may be determined by comparing the characteristics or attributes in a patient's medical records to the characteristics or attributes of the subjects in different studies or clinical trials. In particular, the characteristics or attributes of the patient may be used to determine a search expression that is compared to a corpus of scientific or medical literature to generate match scores (such as a weighted superposition or sum of matches between terms in the search expression and in a particular scientific or medical article or paper), and the relevant scientific or medical papers may be determined based the match scores. The weights used to determine the match scores may be modified based on feedback from the healthcare providers about the relevancy of the displayed scientific or medical papers.

Similarly, the converse contextually sensitive case may also be useful. For example, a healthcare provider may be catching up on scientific or medical papers. While reading a particular article, one or more relevant patients (or links to medical records of the one or more relevant patients) can be displayed for the physician to review. This approach can also assist the healthcare provider in recalling and understanding the scientific or medical literature.

In addition, healthcare providers can create queries of their patients across different risk factors (e.g., blood pressure, body-mass index, age, etc.). Moreover, healthcare providers can create filters that automatically capture specific conditions the healthcare providers look for, and they can share the queries/filters (and, more generally, medical rules) with other healthcare providers at different geographic locations. This may allow the other healthcare providers to run the same queries on their own databases and/or to look for the same characteristics in their patients.

Because the healthcare providers are not sharing PHI, the exchange of these medical rules is anonymous. However, the healthcare providers can collaborate and have a co-anonymized studies of larger populations of subjects, where the identities of the research subjects are protected and only known to their respective healthcare provider. This collaboration may allow each healthcare provider or researcher to only access the medical records of their patients, while allowing them to draw conclusions from a larger pool of relevant data from one or more healthcare providers in their personal and professional networks. In this way, the medical rules can be anonymously shared, and either replicated or refined using additional sub-populations.

In an exemplary embodiment, a healthcare provider can submit a query of risk factors to a patient database. The query may include formal and/or informal questions from the healthcare provider to screen their patients for one or more risk conditions. For example, a query may include looking for patients at risk of heart disease. In particular, the query may look for patients with high blood pressure above a threshold (such as a diastolic blood pressure greater than 88 mm Hg) and a body-mass index above a threshold (such as 25) as being at risk for heart disease. The query may specify blood pressure and body-mass index thresholds that the healthcare provider may want to check up on or review, or may look for new patients who have recently and/or chronically matched the query.

Note that the query can be used once, periodically, or continuously. For example, the computer system may constantly run the query against medical records associated with the healthcare provider. This may involve querying the healthcare provider's medical records using the query to select patients that the healthcare provider wishes to review for a specific health condition. The medical records of the healthcare provider may be constantly updated with new information, including one or more of: lab results (e.g., liquid chromatography-mass spectroscopy (LC-MS) of blood samples, microbiome tests, proteomic tests, genomic tests, etc.), medical imaging results, medical measurement results (such as an MR technique, blood pressure, height, weight, etc.), new family history information, new updates to an invariant MR signature as it is re-run on original MR data collected previously, inputs from radiologists, physicians, nurses and other medical professionals, new research papers entered manually or automatically scraped by a software program, etc. Each time the medical records of the healthcare provider's patients change or are updated, the query can be re-run (constantly or at regular or periodic time intervals) against the medical records, and the analysis results can be updated. Moreover, a new patient who ever matched this query may be returned as additional results to the query. Note that the analysis results for the query may be returned to the computer system for further processing or in order for a notification to be provided to the healthcare provider and/or another healthcare provider.

In particular, the computer system may then provide a notification to the healthcare provider about a new query or analysis results. The query results may include those obtained from the medical records of the healthcare provider's patients and/or any updates or new results to the query. The healthcare provider can receive a notification via a user interface that is displayed on an electronic device. Note that the notification can be transmitted based on a priority level, e.g., an emergency (such as medical images from the last hour that indicate that a patient has a blood clot, LC-MS results from earlier in the day that indicate that a patient has sepsis, etc.), a high priority (such as detection of late-stage cancer, the chemical signature of an illness), a lower priority (such as a patient that is at increased risk over the term for a medical condition), and an ultra-low priority (such as a patient that is in good health, or who has dropped from a high-risk category to a lower risk category). However, these priority levels are for illustrative purposes only, and they may be adjusted or modified based on the healthcare provider's and/or their patients' needs.

Furthermore, the computer system may share the query with another healthcare provider. For example, the healthcare provider may share a query that they run on their own patient medical records with the other healthcare provider. When sharing the query, the healthcare provider may include one or more of: an official name, a nickname, a summary, a research credit, their name, a relevant research paper, anonymized statistics from their own patient medical records, notes, a length of time the query has been used, a time duration since the query was created or first run, and/or other metadata related to the query. In some embodiments, healthcare providers can share their best practices with each other when one of the healthcare providers is starting a new practice. Alternatively or additionally, sharing the query may provide additional analysis (such as a second set of 'virtual eyes') to the other healthcare provider's medical records for their patients without any sharing of medical data and risk of exposure of PHI. Furthermore, the other healthcare provider can either give credit, reference or pay a fee to the other healthcare provider for the use of their queries and filters (and, more generally, medical rules).

The computer system may run the query against the medical records of the patients of the other healthcare provider. This may involve querying the other healthcare provider's medical records using the query to select patients that the other healthcare provider wishes to review for a specific health condition. The medical records of the other healthcare provider may be constantly updated with new information, including one or more of: lab results (e.g., liquid chromatography-mass spectroscopy (LC-MS) of blood samples, microbiome tests, proteomic tests, genomic tests, etc.), medical imaging results, medical measurement results (such as an MR technique, blood pressure, height, weight, etc.), new family history information, new updates to an invariant MR signature as it is re-run on original MR data collected previously, inputs from radiologists, physicians, nurses and other medical professionals, new research papers entered manually or automatically scraped by a software program, etc. Each time the medical records of the other healthcare provider's patients change or are updated, the query can be re-run (constantly or at regular or periodic time intervals) against the medical records, and the analysis results can be updated. Moreover, a new patient who ever matched this query may be returned as additional results to the query. Note that the analysis results for the query may be returned to the computer system for further processing or in order for a notification to be provided to the other healthcare provider and/or the healthcare provider.

Thus, the computer system may then provide a notification to the other healthcare provider about the query or analysis results. The query results may include those obtained from the medical records of the other healthcare provider's patients and/or any updates or new results to the query. The other healthcare provider can receive a notification via a user interface that is displayed on an electronic device. Note that the notification can be transmitted based on a priority level, e.g., an emergency (such as medical images from the last hour that indicate that a patient has a blood clot, LC-MS results from earlier in the day that indicate that a patient has sepsis, etc.), a high priority (such as detection of late-stage cancer, the chemical signature of an illness), a lower priority (such as a patient that is at increased risk over the term for a medical condition), and an ultra-low priority (such as a patient that is in good health, or who has dropped from a high-risk category to a lower risk category). However, these priority levels are for illustrative purposes only, and they may be adjusted or modified based on the other healthcare provider's and/or their patients' needs.

Furthermore, the computer system may optionally compile a co-anonymized study from both healthcare providers across both of their patients' medical records. This co-anonymized study may include the results from one or more healthcare providers using the same query across their datasets to measure the statistical significance of a categorical or a quantitative hypothesis across a larger sample than each individual healthcare provider would have access to on their own. Moreover, the analysis results may be computed from a larger anonymous population (e.g., each healthcare provider can view their own patients' identities, but cannot access or view the identities of the rest of the sub-populations that belongs to their collaborators). The analysis results can be published in peer-reviewed journals and/or unofficially as an ongoing experiment or best practice that is shared among the healthcare providers who can continually monitor the results and the accuracy of their hypotheses. This capability enables a new way of producing, testing and using medical studies of various levels of formality, and enables studies of both common diseases and rare or 'orphan' diseases by groups of healthcare providers. Thus, the analysis technique may enable better healthcare and healthcare outcomes for patients.

In another exemplary embodiment, contextually sensitive notifications are used to show healthcare providers which of their patients are relevant to medical literature they are reviewing. Alternatively, contextually sensitive notifications may be used to show healthcare provider which medical articles or papers are relevant to their patients.

For example, the computer system may receive a request, from a healthcare provider, for medical information of a patient. The request can be generated during a patient visit, during a healthcare-provider review of patient medical records, during a query run on a set of medical records looking for patients with a specific set of risk factors, in response to new medical information entered into medical records associated with patients of the healthcare provider, etc.

In response, the computer system may query a corpus of scientific or medical literature using one or more parameters or characteristics from the patient information (such as by generating match scores based on a search expression), and may receive a list of literature relevant to the patient. Note that the parameters can be specified by the healthcare provider and/or can be determined from parameters referenced in the scientific or medical literature. For example, the scientific or medical literature can reference patients with a blood pressure above a threshold and a body-mass index above a threshold as having a risk of heart disease. This information can be used to determine query results, such as identifying a patient with those characteristics (such as blood pressure and a body-mass index above their respective thresholds). Moreover, the lists of relevant literature (or information that specifies the relevant literature) may include: an unordered list, an ordered list (such as a ranking based on a match or relevancy score, disease type, disease severity, data of discovery, etc.), or another data structure.

Then, the computer system may display or present to the healthcare provider the patient medical information and the identified relevant literature. For example, the relevant literature may be displayed in a user interface alongside, above, below, on a notification menu on a status bar, using a notification icon, etc. In some embodiments, the relevant papers can be displayed using small summaries or thumbnails, which can include: a title, date of publication, a ranking, a prioritization (such as based on the seriousness of a disease), and/or any other suitable metadata.

In some embodiments, the computer system may receive, from the healthcare provider, feedback about the relevancy of the literature, which can be used to modify or adapt the generation of the match scores (such as weights used to generate the match scores). This may improve the accuracy of identified relevant literature in the future. For example, the feedback may be explicit, such as by providing a feedback score using binary, categorical or quantitative icons in a user interface. In particular, the icons may be: binary (such as 'relevant' or 'not relevant'), a ranking from 1-5, etc. Alternatively, the feedback may be implicit, such as by monitoring clicks (e.g., if a healthcare provider clicks on an article, it may be considered to be a relevant article or scientific study). Note that the healthcare provider may select reminders for the relevancy of a particular scientific paper, may whitelist the scientific paper, or may block a scientific paper from a recommendation engine (such as a blacklist) in order to improve their user experience.

Similarly, after receiving a healthcare-provider request for scientific or medical literature, the computer system may query the medical records of patients using one or more parameters from the scientific or medical literature. For example, the scientific paper can be a medical study and/or in any suitable journal or online publication related to medicine (such as microbiology, healthcare economics and administration, physics, chemistry, biology, anthropology, sociology, psychology, etc.). The request may be generated: during a literature review session (such as where a healthcare provider is studying the latest techniques and advances in the field), during a patient visit, during a healthcare-provider review of patient medical records, during a query run on a corpus of scientific literature looking for interesting articles, etc.

Moreover, the computer system may query a set of medical records using one or more parameters or characteristics from the scientific or medical literature. The characteristics/parameters may be specified by the healthcare provider and/or may be determined from parameters referenced in the scientific or medical literature. For example, the scientific or medical literature may reference patients with a blood pressure above a threshold and a body-mass index above a threshold as having a risk of heart disease. In response, the query results may include or specify patients with specific risk factors or characteristics (such as blood pressure and body-mass index above their respective thresholds).

Next, the computer system may receive a list of relevant patients. This list may include: an unordered list, an ordered list (such as a ranking based on relevancy or matching scores, a ranking based on a risk of disease, a ranking based on a seriousness of disease, a ranking based on a date of last patient visit, etc.), or another data structure.

Then, the computer system may display the list to the healthcare provider. For example, the relevant patients may be displayed in a user interface alongside, above, below, on a notification menu on a status bar, using a notification icon, etc. In some embodiments, the relevant patients can be displayed using small summaries or thumbnails, which can include: a ranking, a prioritization (such as based on the seriousness of a disease, a last patient visit, etc.), and/or any other suitable metadata.

In some embodiments, the computer system may receive, from the healthcare provider, relevancy feedback for at least one of the listed patients, which can be used to modify or adapt the generation of the match scores (such as weights used to generate the match scores). This may improve the accuracy of identified relevant patients in the future. For example, the feedback may be explicit, such as by providing a feedback score using binary, categorical or quantitative icons in a user interface. In particular, the icons may be: binary (such as 'relevant' or 'not relevant'), a ranking from 1-5, etc. Alternatively, the feedback may be implicit, such as by monitoring clicks (e.g., if a healthcare provider clicks on a patient, they may be considered to be a relevant patient). Note that the healthcare provider may select reminders for the relevancy of a particular patient, may whitelist the patient, or may block a patient from a recommendation engine (such as a blacklist) in order to improve their user experience.

Figure 4:
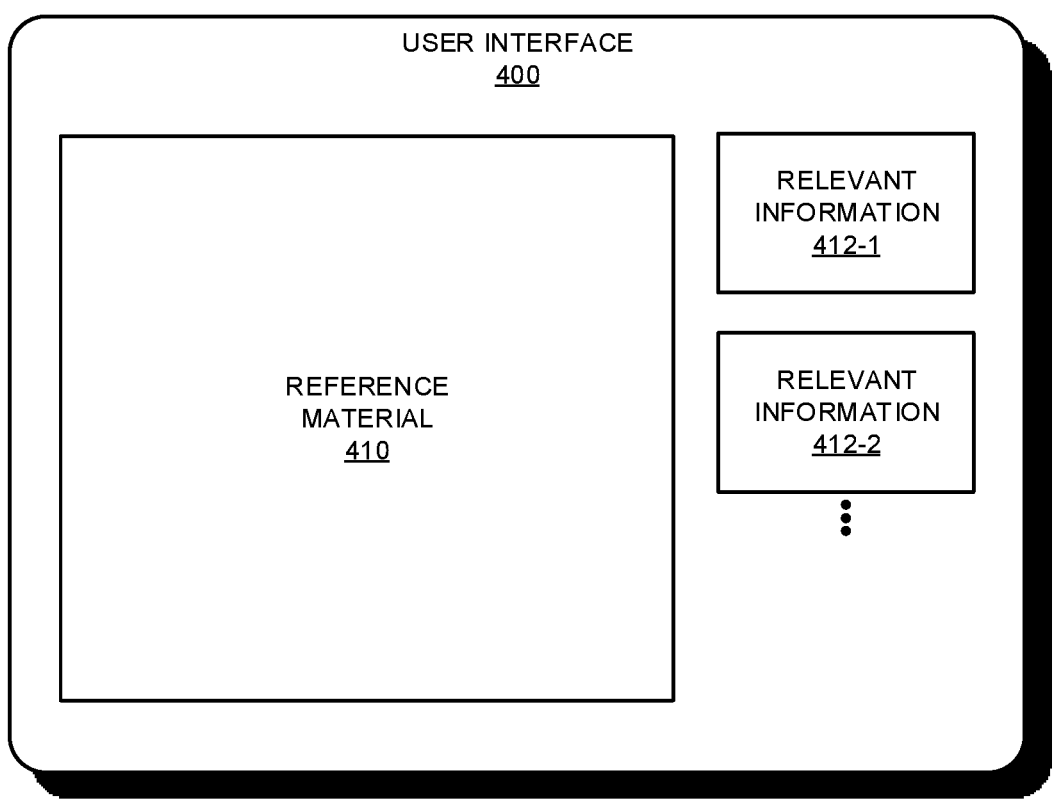
FIG. 4 is a drawing illustrating a user interface in the system of FIG. 1 in accordance with an embodiment of the present disclosure.

FIG. 4 presents a drawing illustrating a user interface 400 in system 100 (FIG. 1). This user interface may include reference material 410, such as patient information, or scientific or medical articles. In addition, user interface 400 may include relevant information 412, such as a list of relevant scientific or medical articles, or a list of relevant patients.

As described previously, in some embodiments the results from a co-anonymous study may be used to adapt or modify a local medical rule to generate a population-based medical rule. For example, hypothesis testing based on a contingency table or another suitable statistical analysis technique may be used to confirm whether or not a local medical rule is statistically significant (such as a p-value of 0.1., 1 or 5%) relative to a null hypothesis. If yes, the local medical rule may be confirmed as a population-based medical rule. Alternatively, if the local medical rule is not statistically significant, the local medical rule may be deemed invalid (at least at the time of the analysis) and the population-based medical rule may indicate that the local medical rule should not be used until further notice.

In some embodiments, adapting or modifying the local medical rule to generate the population-based medical rule involves quantitative changes to a threshold or a numerical value in the local medical rule. For example, the analysis results from one or more additional sub-populations may be used in conjunction with a numerical technique, such as: Newton's method, least squares, support vector machines, classification and regression trees, a neural network, logistic regression, linear regression, nonlinear regression, a Bayesian technique and/or another supervised learning technique.

Furthermore, in some embodiments adapting or modifying the local medical rule to generate the population-based medical rule involves changing operations or reordering operations in a diagnostic technique or a treatment technique. The changes or reordering may be based on numerical analysis of the analysis results (e.g., without user input) and/or may be based on user input.

Additionally, in some embodiments the computer system re-analyzes a predetermined invariant signature based on a medical rule. For example, the computer system may re-analyzes the predetermined invariant signature based on a modified measurement configuration (which is determined from or specified by the medical rule) to generate simulated data. In particular, the invariant MR signature may be based on an MR model of the dynamic response of voxels in a biological organism to an external magnetic field and measurement conditions that are described or specified in scanning instructions in the measurement configuration (e.g., magnetic-field strengths, pulse sequences, the voxel size, one or more spectra, one or more types of nuclei, etc.). Stated differently, the MR model may accurately predict MR signal evolution or response for the voxels in the biological organism over a range of parameters ($T_1$, $T_2$, proton density, off-resonances, environment, location, temperature, pulse sequences, etc.) using the Bloch equations, full Liouvillian computations or another simulation technique.

Using the Bloch equations as an illustrative example, the MR model may be a 3D model of voxels in at least a portion of a biological organism (and, more generally, the biological organism), and may include parameters in the Bloch equations for each of the voxels. In particular, with a quasi-static magnetic field $B_0$ along the z axis, the Bloch equations are $$\frac{dM_x(t)}{dt} = \gamma \cdot (\vec{M}(t) \otimes \vec{B}(t))_x - \frac{M_x(t)}{T_2},$$

$$\frac{dM_y(t)}{dt} = \gamma \cdot (\vec{M}(t) \otimes \vec{B}(t))_y - \frac{M_y(t)}{T_2}, \text{ and}$$

$$\frac{dM_z(t)}{dt} = \gamma \cdot (\vec{M}(t) \otimes \vec{B}(t))_z - \frac{M_z(t) - M_0}{T_1},$$

where $\gamma$ is the gyromagnetic ratio, $\otimes$ denotes a vector cross product and $\vec{B}(t)=(B_x(t), B_y(t), B_0+\Delta B_z(t))$ is the magnetic field experienced by a type of nuclei in the biological organism. The parameters in the Bloch equations may include $T_1$, $T_2$, a density of a type of nuclei, diffusion, velocity/flow, temperature, and magnetic susceptibility. Note that there may be different parameters for different types of nuclei for each of the voxels. Moreover, note that the Bloch equations are a semi-classical, macroscopic approximation to the dynamic response of the magnetic moments of the type of nuclei in the biological organism to a time-varying magnetic field. For example, there may be 67 M cells in a 1 mm$^3$ voxel.

The invariant MR signature may include 'surface signatures,' as opposed to 1D signatures. For example, using measurements at multiple magnetic-field strengths or in the presence of known magnetic-field disturbances (such as rotation), a set of MR trajectories that may be used to determine the invariant MR signature(s). Note that each MR trajectory may be defined by a magnetic-field function rather than a fixed magnetic-field strength.

Additionally, the MR model may include simulations of dynamics, such as motion associated with: respiration, a heartbeat, blood flow, mechanical motion, etc. (Thus, there may be additional terms in the Bloch equations for diffusion, thermometry, spectroscopy, elastography, etc. Consequently, the MR model may be based on the Bloch-Torrey equations, etc.) For example, when a voxel contains a space that has a fluid flowing through it (such as in a vein), the flow of the liquid may be simulated by building a map of the flow directions and velocity magnitudes in the biological organism being scanned so that this information may be accounted for in the invariant MR signature. Furthermore, when scanning a human or an animal, the MR model may include the resting motion (such as that associated with respiration, a heartbeat, etc.).

The MR model may be used to predict how the biological organisms will respond to particular scanning instructions or a measurement configuration. In particular, the MR model may be used to simulate or estimate the MR signals for a particular MR scanner having particular characteristics, for particular scanning instructions and/or for a particular biological organism (which may have a medical history, previous MR scan results, patterns of breathing, patterns of movement, etc.). Stated different, an invariant MR signature (which is based on the MR model) may be used to determine representations or projections (i.e., the MR signals) in particular contexts, such as based on the particular characteristics of the MR scanner, the particular scanning instructions and/or the particular biological organism.

Thus, the MR model may have been determined using active learning. In particular, the MR model may be iteratively fit or determined based on 'queries' generated by a learning system or a learning engine (which may be implemented in computer system 114 in FIG. 1). The queries generated by the learning engine may include different magnetic-field strengths $B_0$, different electromagnetic pulse sequences and/or different ultrasonic pulse sequences that are based on confidence intervals for parameters in the MR model. Consequently, the learning engine may use the measured MR signals in response to these queries to determine unknown parameters in the MR model and/or parameters having a poor accuracy (such as a confidence interval greater than 0.1 1, 5 or 10%). More generally, the adaptive learning may be based on a wide variety of measurements, such as optical/infrared spectroscopy, x-ray, computed tomography, proton beam, photoacoustic, ultrasound, etc.

While the preceding discussion used the Bloch equations as an illustrative example, in other embodiments full Liouvillian computations (such as a Liouville supermatrix of interactions between two or more elements) or another simulation technique are used. Note that the MR signals computed or predicted using the MR model may be sampled at a rate equal to or higher than twice the Nyquist frequency of MR signals acquired during an MR scan.

Figure 5:
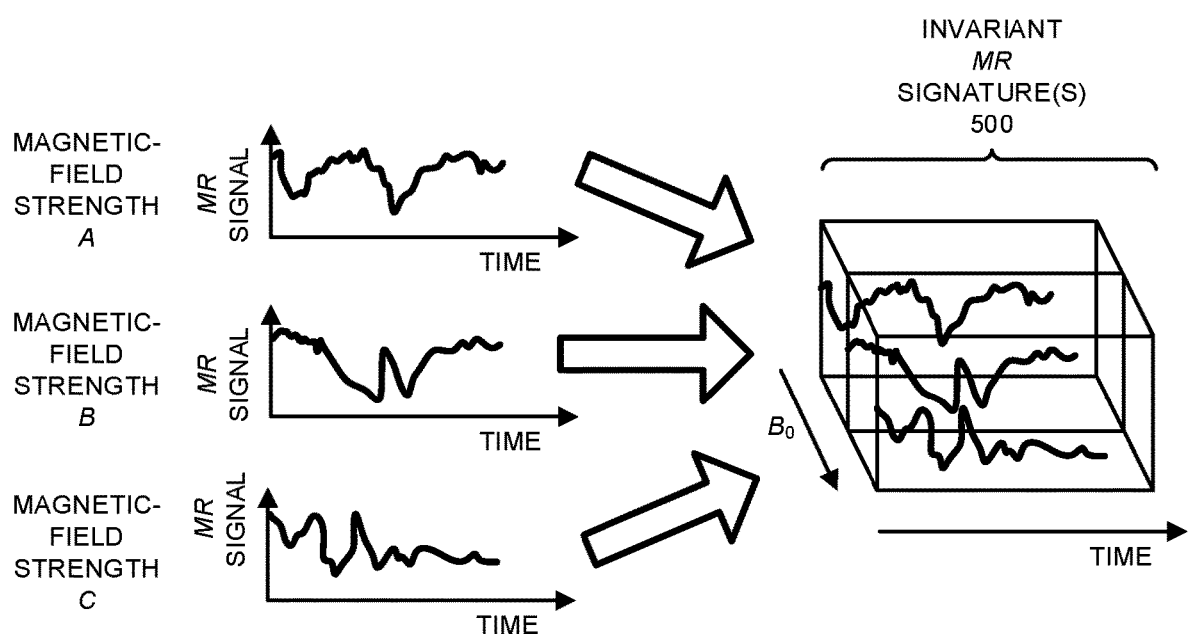
FIG. 5 is a drawing illustrating an invariant magnetic-resonance (MR) signature that specifies the response to a surface of magnetic-field strengths in accordance with an embodiment of the present disclosure.

FIG. 5, which presents a drawing illustrating an invariant MR signature that specifies the response to a surface of magnetic-field strengths, summarizes the preceding discussion of parameters for one or more MR models that accurately predict MR signals. In particular, MR signals or trajectories acquired at different magnetic-field strengths may be combined into a set of MR signals that specify the response to the surface of magnetic-field strengths. This response may be used to determine one or more invariant MR signatures 500.

We now describe embodiments of an electronic device. FIG. 6 presents a block diagram illustrating an electronic device 600, such as one of electronic devices 110 or computer system 118 in FIG. 1. This electronic device includes processing subsystem 610, memory subsystem 612, and networking subsystem 614. Processing subsystem 610 includes one or more devices configured to perform computational operations. For example, processing subsystem 610 can include one or more microprocessors, application-specific integrated circuits (ASICs), microcontrollers, programmable-logic devices, and/or one or more digital signal processors (DSPs).

Memory subsystem 612 includes one or more devices for storing data and/or instructions for processing subsystem 610 and networking subsystem 614. For example, memory subsystem 612 can include dynamic random access memory (DRAM), static random access memory (SRAM), and/or other types of memory. In some embodiments, instructions for processing subsystem 610 in memory subsystem 612 include: one or more program modules or sets of instructions (such as program module 622 or operating system 624), which may be executed by processing subsystem 610. Note that the one or more computer programs may constitute a computer-program mechanism. Moreover, instructions in the various modules in memory subsystem 612 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 610.

In addition, memory subsystem 612 can include mechanisms for controlling access to the memory. In some embodiments, memory subsystem 612 includes a memory hierarchy that comprises one or more caches coupled to a memory in electronic device 600. In some of these embodiments, one or more of the caches is located in processing subsystem 610.

In some embodiments, memory subsystem 612 is coupled to one or more high-capacity mass-storage devices (not shown). For example, memory subsystem 612 can be coupled to a magnetic or optical drive, a solid-state drive, or another type of mass-storage device. In these embodiments, memory subsystem 612 can be used by electronic device 600 as fast-access storage for often-used data, while the mass-storage device is used to store less frequently used data.

Figure 6:
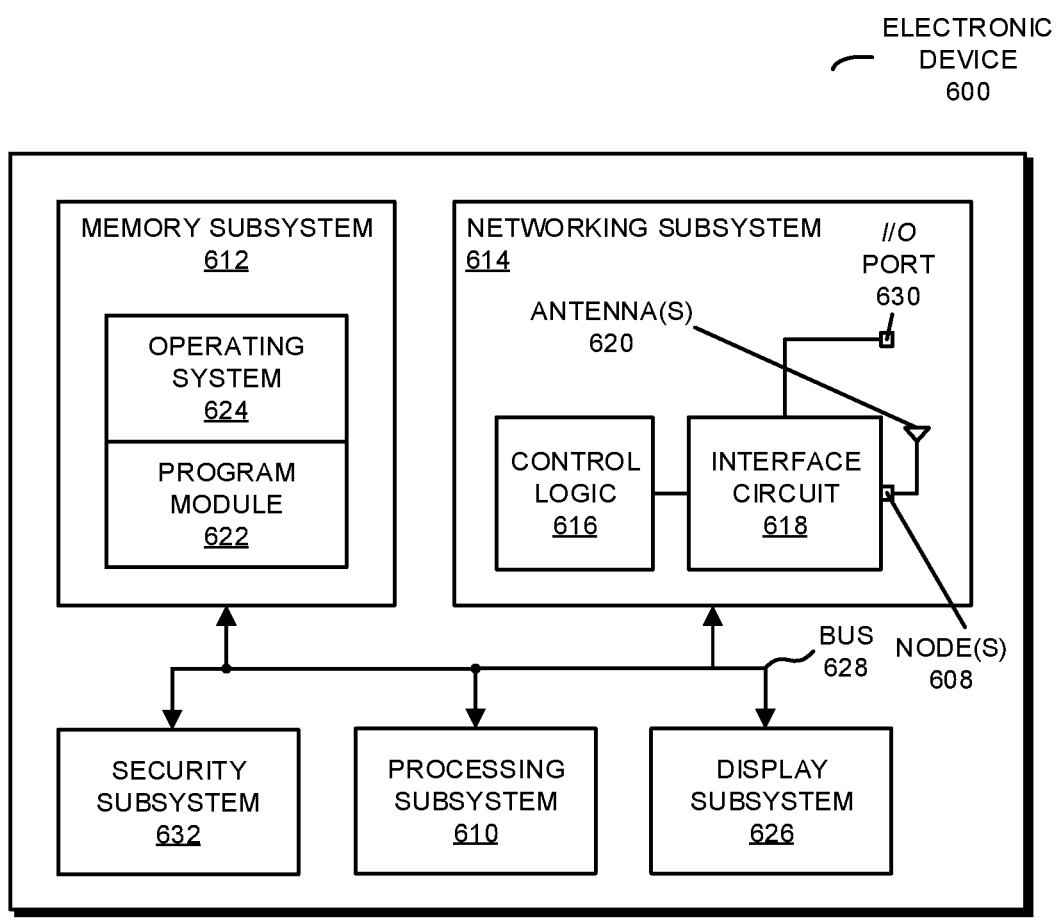
FIG. 6 is a block diagram illustrating an electronic device in the system of FIG. 1 in accordance with an embodiment of the present disclosure.

While FIG. 6 illustrates electronic device 600 as including memory subsystem 612, in some embodiments memory subsystem 612 includes remotely accessible memory, such as: a cloud-based storage system, a high-capacity network attached mass-storage device (e.g., network attached storage), an external hard drive, a magnetic-tape backup system, a medical records archive service, or any other suitable archive devices.

In some embodiments, blocks of data are stored in memory subsystem 612 using a blockchain or similar cryptographic hash technology to detect unauthorized modification or corruption of records. Moreover, the data can be anonymized so that the identity associated with a subject is anonymous unless the subject gives permission or authorization for this information to be released.

Figure 7:
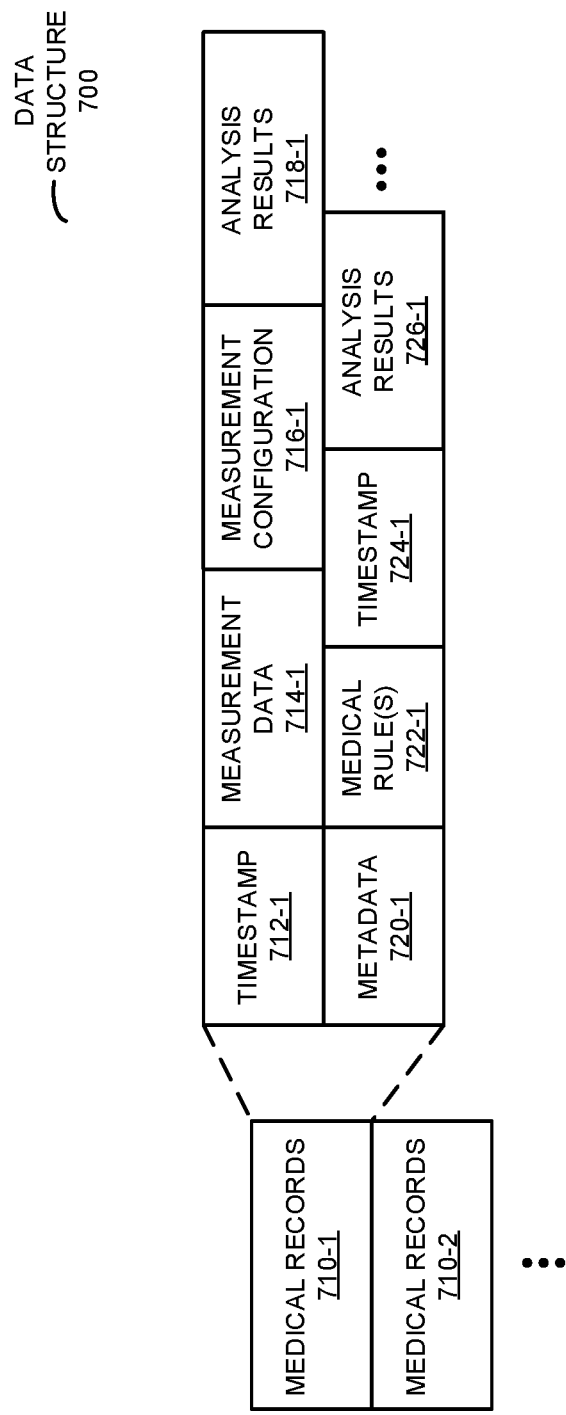
FIG. 7 is a drawing illustrating a data structure for use in the electronic device of FIG. 6 in accordance with an embodiment of the present disclosure.

Moreover, memory subsystem 612 may store or may have access to medical records for one or more patients that are associated with one or more healthcare providers. FIG. 7 presents a drawing illustrating a data structure 700 for use in electronic device 600 (FIG. 6). In particular, data structure 700 may include medical records 710 for different patients or individuals. These medical records may include: timestamps 712 when the measurements were performed, measurement data 714, measurement configurations 716, analysis results 718 and optional patient metadata 720. As described previously, the inclusion of separate measurement data 714 and measurement configurations 716 may facilitate retrospective analysis of the medical records 710 at subsequent time stamps 724 based on one or more medical rules 722 to determine new or revised analysis results 726.

Referring back to FIG. 6, networking subsystem 614 may include one or more devices configured to couple to and communicate on a wired and/or wireless network (i.e., to perform network operations), including: control logic 616, an interface circuit 618, one or more antennas 620 and/or input/output (I/O) port 630. (While FIG. 6 includes one or more antennas 620, in some embodiments electronic device 600 includes one or more nodes 608, e.g., a pad, which can be coupled to one or more antennas 620. Thus, electronic device 600 may or may not include one or more antennas 620.) For example, networking subsystem 614 can include a Bluetooth networking system, a cellular networking system (e.g., a 3G/4G network such as UMTS, LTE, etc.), a universal serial bus (USB) networking system, a networking system based on the standards described in IEEE 802.11 (e.g., a Wi-Fi networking system), an Ethernet networking system, and/or another networking system.

Networking subsystem 614 includes processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for the network system. Moreover, in some embodiments a 'network' between the electronic devices does not yet exist. Therefore, electronic device 600 may use the mechanisms in networking subsystem 614 for performing simple wireless communication between the electronic devices, e.g., transmitting advertising or beacon frames and/or scanning for advertising frames transmitted by other electronic devices as described previously.

Within electronic device 600, processing subsystem 610, memory subsystem 612, and networking subsystem 614 are coupled together using bus 628. Bus 628 may include an electrical, optical, and/or electro-optical connection that the subsystems can use to communicate commands and data among one another. Although only one bus 628 is shown for clarity, different embodiments can include a different number or configuration of electrical, optical, and/or electro-optical connections among the subsystems.

In some embodiments, electronic device 600 includes a display subsystem 626 for displaying information on a display, which may include a display driver and the display, such as: a liquid-crystal display, a multi-touch touchscreen or a touch-sensitive display, an optical projector, a laser projector, a holographic display, or any other suitable display for displaying 2-dimensional or 3-dimensional images.

Moreover, electronic device 600 may include a security subsystem 632, which may include one or more biometric sensor(s) and/or may implement password authorization. For example, the one or more biometric sensors may include: a fingerprint scanner, a retina scanner, and/or another biometric sensor that can capture biometric information that is used for authentication and/or authorization.

Electronic device 600 can be (or can be included in) any electronic device with at least one network interface. For example, electronic device 600 can be (or can be included in): a desktop computer, a laptop computer, a subnotebook/netbook, a server, a workstation, a tablet computer, a smartphone, a cellular telephone, a smart watch, a consumer-electronic device, a portable computing device, an access point, a router, a switch, communication equipment, test equipment, a wearable appliance, and/or another electronic device.

Although specific components are used to describe electronic device 600, in alternative embodiments, different components and/or subsystems may be present in electronic device 600. For example, electronic device 600 may include one or more additional processing subsystems, memory subsystems, networking subsystems, display subsystems and/or audio subsystems. Additionally, one or more of the subsystems may not be present in electronic device 600. Moreover, in some embodiments, electronic device 600 may include one or more additional subsystems that are not shown in FIG. 6. Also, although separate subsystems are shown in FIG. 6, in some embodiments, some or all of a given subsystem or component can be integrated into one or more of the other subsystems or component(s) in electronic device 600. For example, in some embodiments program module 622 is included in operating system 624.

Moreover, the circuits and components in electronic device 600 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 614, such as a radio. Moreover, the integrated circuit may include hardware and/or software mechanisms that are used for transmitting wireless signals from electronic device 600 and receiving signals at electronic device 600 from other electronic devices. Aside from the mechanisms herein described, radios are generally known in the art and hence are not described in detail. In general, networking subsystem 614 and/or the integrated circuit can include any number of radios. Note that the radios in multiple-radio embodiments function in a similar way to the described single-radio embodiments.

In some embodiments, networking subsystem 614 and/or the integrated circuit include a configuration mechanism (such as one or more hardware and/or software mechanisms) that configures the radio(s) to transmit and/or receive on a given communication channel (e.g., a given carrier frequency). For example, in some embodiments, the configuration mechanism can be used to switch the radio from monitoring and/or transmitting on a given communication channel to monitoring and/or transmitting on a different communication channel. (Note that 'monitoring' as used herein comprises receiving signals from other electronic devices and possibly performing one or more processing operations on the received signals, e.g., determining if the received signal comprises an advertising frame, receiving the input data, etc.)

While communication protocols compatible with Ethernet and Wi-Fi or a cellular-telephone communication protocol were used as illustrative examples, the described embodiments of the analysis technique may be used in a variety of network interfaces. Furthermore, while some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both. For example, at least some of the operations in the analysis technique may be implemented using program module 622, operating system 624 (such as a driver for interface circuit 618) and/or in firmware in interface circuit 618. Alternatively or additionally, at least some of the operations in the analysis technique may be implemented in a physical layer, such as hardware in interface circuit 618.

While program module 622 is illustrated as being resident on and executed by electronic device 600, in some embodiments a user of electronic device 600 may interact with a web page that is provided by another electronic device, and which is rendered by a web browser on electronic device 600. In some embodiments, at least a portion of program module 622 (such as software or an application) executing on electronic device 600 may be an application tool that is embedded in the web page, and that executes in a virtual environment of the web browser. Thus, the application tool may be provided to the user via a client-server architecture. Note that program module 622 executed by electronic device 600 may be a standalone application or a portion of another application that is resident on and that executes on electronic device 600.

In the preceding description, we refer to 'some embodiments.' Note that 'some embodiments' describes a subset of all of the possible embodiments, but does not always specify the same subset of embodiments. Moreover, note that the numerical values provided are intended as illustrations of the communication technique. In other embodiments, the numerical values can be modified or changed.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A method for dynamically generating a population-based medical rule via anonymous sharing of a local medical rule, comprising:

by a processor:

receiving, from a user, information specifying the local medical rule associated with an initial sub-population and sharing instructions that specify other users that can access the local medical rule;

iteratively:

applying the local medical rule to one or more additional sub-populations without sharing Protected Health Information (PHI) associated with the initial sub-population, wherein the one or more additional sub-populations are associated with at least some of the other users, wherein applying the local medical rule to one or more additional sub-populations comprises retrospective analysis using medical records associated with the one or more additional sub-populations, the retrospective analysis comprises reanalyzing previously acquired measurements based at least in part on a change to a stored measurement configuration that was used to acquire the measurements, the change corresponding to the local medical rule, and the reanalyzing comprises determining simulated magnetic-resonance (MR) signals based at least in part on a MR model of one or more types of nuclei in voxels at three-dimensional (3D) positions in at least portions of individuals in the one or more additional sub-populations, voxel parameters, and a magnetic-field direction, a magnetic-field strength and a pulse sequence specified by the change to the stored measurement configuration, and wherein determining the MR signals comprises simulating MR physics in at least the portions of the individuals using Bloch equations or Liouvillian computations, and the voxel parameters comprise a spin-lattice relaxation time along a direction parallel to the magnetic-field direction, a spin-spin relaxation time along a direction transverse to the magnetic-field direction, and one or more densities of the one or more types of nuclei;

aggregating results associated with the local medical rule for the one or more additional sub-populations; and generating the population-based medical rule by modifying the local medical rule based on the aggregated results and one or more quality metrics; and after generating the population-based medical rule, selectively providing the population-based medical rule to the user without sharing PHI associated with the one or more additional sub-populations.

2. The method of claim 1, wherein applying the local medical rule to the one or more additional sub-populations comprises using the local medical rule during future clinical encounters with individuals in the one or more additional sub-populations.

3. The method of claim 1, wherein the local medical rule comprises at least one of: one or more diagnostic criteria, and a treatment protocol.

4. The method of claim 1, wherein the operations of applying, aggregating and generating are performed continuously or periodically for the population-based medical rule.

5. The method of claim 1, wherein selectively providing the population-based medical rule comprises providing a notification to the user.

6. The method of claim 1, wherein the method further comprises:

providing, to the other users, notifications about the local medical rule in response to the sharing instructions; and in response to receiving an opt-in instruction from one of the other users, including a particular sub-population in the one or more additional sub-populations.

7. The method of claim 1, wherein the user and the other users comprise at least one of: healthcare providers, and healthcare researchers.

8. The method of claim 1, wherein the local medical rule comprises a query.

9. The method of claim 1, wherein the population-based medical rule is editable; and wherein the method further comprises, when an editing instruction for the population-based medical rule is received from another user, retroactively applying the revised population-based medical rule to medical records associated with at least one of: the initial sub-population, and the one or more additional sub-populations.

10. The method of claim 1, wherein the population-based medical rule is editable; and wherein the method further comprises:

when an editing instruction for the population-based medical rule is received from another user, prospectively applying the revised population-based medical rule during further clinical encounters with individuals in at least one of: the initial sub-population, and the one or more additional sub-populations; and aggregating second results associated with the revised population-based medical rule; and determining an updated population-based medical rule based on the aggregated second results and the one or more quality metrics.

11. A non-transitory computer-program product for use in conjunction with a computer system, the computer-program product comprising instructions for dynamically generating a population-based medical rule via anonymous sharing of a local medical rule, the instructions, when the executed by a processor in the computer system, cause the computer system to:

receiving, from a user, information specifying the local medical rule associated with an initial sub-population and sharing instructions that specify other users that can access the local medical rule;

iteratively:

applying the local medical rule to one or more additional sub-populations without sharing Protected Health Information (PHI) associated with the initial sub-population, wherein the one or more additional sub-populations are associated with at least some of the other users, wherein applying the local medical rule to one or more additional sub-populations comprises retrospective analysis using medical records associated with the one or more additional sub-populations, the retrospective analysis comprises reanalyzing previously acquired measurements based at least in part on a change to a stored measurement configuration that was used to acquire the measurements, the change corresponding to the local medical rule, and the reanalyzing comprises determining simulated magnetic-resonance (MR) signals based at least in part on a MR model of one or more types of nuclei in voxels at three-dimensional (3D) positions in at least portions of individuals in the one or more additional sub-populations, voxel parameters, and a magnetic-field direction, a magnetic-field strength and a pulse sequence specified by the change to the stored measurement configuration, and wherein determining the MR signals comprises simulating MR physics in at least the portions of the individuals using Bloch equations or Liouvillian computations, and the voxel parameters comprise a spin-lattice relaxation time along a direction parallel to the magnetic-field direction, a spin-spin relaxation time along a direction transverse to the magnetic-field direction, and one or more densities of the one or more types of nuclei;

aggregating results associated with the local medical rule for the one or more additional sub-populations; and generating the population-based medical rule by modifying the local medical rule based on the aggregated results and one or more quality metrics; and after generating the population-based medical rule, selectively providing the population-based medical rule to the user without sharing PHI associated with the one or more additional sub-populations.

12. The computer-program product of claim 11, wherein applying the local medical rule to the one or more additional sub-populations comprises using the local medical rule during future clinical encounters with individuals in the one or more additional sub-populations.

13. The computer-program product of claim 11, wherein executing the instructions further causes the computer system to:
provide, to the other users, notifications about the local medical rule in response to the sharing instructions; and
in response to receiving an opt-in instruction from one of the other users, include a particular sub-population in the one or more additional sub-populations.

14. The computer-program product of claim 11, wherein the local medical rule comprises a query.

15. The computer-program product of claim 11, wherein the population-based medical rule is editable; and
wherein executing the instructions further causes the computer system to, when an editing instruction for the population-based medical rule is received from another user, retroactively apply the revised population-based medical rule to medical records associated with at least one of: the initial sub-population, and the one or more additional sub-populations.

16. The computer-program product of claim 11, wherein the population-based medical rule is editable; and
wherein executing the instructions further causes the computer system to:
when an editing instruction for the population-based medical rule is received from another user, prospectively apply the revised population-based medical rule during further clinical encounters with individuals in at least one of: the initial sub-population, and the one or more additional sub-populations; and
aggregate second results associated with the revised population-based medical rule; and
determine an updated population-based medical rule based on the aggregated second results and the one or more quality metrics.

17. A computer system, comprising:
a processor configured to execute a program module;
memory, coupled to the processor, configured to store instructions for dynamically generating a population-based medical rule via anonymous sharing of a local medical rule, wherein, when executed by the processor, the instructions cause the computer system to:
receive, from a user, information specifying the local medical rule associated with an initial sub-population and sharing instructions that specify other users that can access the local medical rule;
iteratively:
apply the local medical rule to one or more additional sub-populations without sharing Protected Health Information (PHI) associated with the initial sub-population, wherein the one or more additional sub-populations are associated with at least some of the other users, wherein applying the local medical rule to one or more additional sub-populations comprises retrospective analysis using medical records associated with the one or more additional sub-populations, the retrospective analysis comprises reanalyzing previously acquired measurements based at least in part on a change to a stored measurement configuration that was used to acquire the measurements, the change corresponding to the local medical rule, and the reanalyzing comprises determining simulated magnetic-resonance (MR) signals based at least in part on a MR model of one or more types of nuclei in voxels at three-dimensional (3D) positions in at least portions of individuals in the one or more additional sub-populations, voxel parameters, and a magnetic-field direction, a magnetic-field strength and a pulse sequence specified by the change to the stored measurement configuration, and wherein determining the MR signals comprises simulating MR physics in at least the portions of the individuals using Bloch equations or Liouvillian computations, and the voxel parameters comprise a spin-lattice relaxation time along a direction parallel to the magnetic-field direction, a spin-spin relaxation time along a direction transverse to the magnetic-field direction, and one or more densities of the one or more types of nuclei;
aggregate results associated with the local medical rule for the one or more additional sub-populations; and
generate the population-based medical rule by modifying the local medical rule based on the aggregated results and one or more quality metrics; and
after generating the population-based medical rule, selectively providing the population-based medical rule to the user without sharing PHI associated with the one or more additional sub-populations.

18. The computer of claim 17, wherein applying the local medical rule to the one or more additional sub-populations comprises using the local medical rule during future clinical encounters with individuals in the one or more additional sub-populations.

19. The computer of claim 17, wherein the population-based medical rule is editable; and
wherein executing the instructions further causes the computer system to, when an editing instruction for the population-based medical rule is received from another user, retroactively apply the revised population-based medical rule to medical records associated with at least one of: the initial sub-population, and the one or more additional sub-populations.

20. The computer of claim 17, wherein the population-based medical rule is editable; and
wherein executing the instructions further causes the computer system to:
when an editing instruction for the population-based medical rule is received from another user, prospectively apply the revised population-based medical rule during further clinical encounters with individuals in at least one of: the initial sub-population, and the one or more additional sub-populations; and
aggregate second results associated with the revised population-based medical rule; and
determine an updated population-based medical rule based on the aggregated second results and the one or more quality metrics.

* * * * *